(12) United States Patent
Cuzner et al.

(10) Patent No.: US 12,127,893 B2
(45) Date of Patent: Oct. 29, 2024

(54) SUPPORT ARM APPARATUS FOR SUPPORTING MEDICAL INSTRUMENT

(71) Applicant: Magassist, Inc., Jiangsu (CN)

(72) Inventors: Robert Cuzner, Jiangsu (CN); Davis Tolley, Jiangsu (CN); Kynan Taylor, Jiangsu (CN); Polin Hsu, Jiangsu (CN); Ifan Yen, Jiangsu (CN)

(73) Assignee: Magassist, Inc., Jiangsu (CN)

( * ) Notice: Subject to any disclaimer, the term of this patent is extended or adjusted under 35 U.S.C. 154(b) by 656 days.

(21) Appl. No.: 17/424,831

(22) PCT Filed: Jan. 17, 2020

(86) PCT No.: PCT/CN2020/072579
§ 371 (c)(1),
(2) Date: Oct. 26, 2021

(87) PCT Pub. No.: WO2020/151575
PCT Pub. Date: Jul. 30, 2020

(65) Prior Publication Data
US 2022/0047352 A1    Feb. 17, 2022

(30) Foreign Application Priority Data

Jan. 23, 2019  (CN) .......................... 201910061209.1

(51) Int. Cl.
*A61B 90/50*   (2016.01)
*F16M 11/14*   (2006.01)

(52) U.S. Cl.
CPC ............. *A61B 90/50* (2016.02); *F16M 11/14* (2013.01); *F16M 2200/022* (2013.01)

(58) Field of Classification Search
CPC ... F16M 11/14; F16M 2200/022; A61B 90/50
See application file for complete search history.

(56) References Cited

U.S. PATENT DOCUMENTS

| 4,491,435 A | * | 1/1985 | Meier ................ F16M 11/2078 403/56 |
| 5,020,933 A | * | 6/1991 | Salvestro ........... F16M 11/2078 403/90 |

(Continued)

FOREIGN PATENT DOCUMENTS

| CN | 1969772 A | 5/2007 |
| CN | 104736077 A | 6/2015 |

(Continued)

*Primary Examiner* — Monica E Millner
(74) *Attorney, Agent, or Firm* — Flaster Greenberg P.C.

(57) ABSTRACT

The present invention relates to a support arm apparatus for supporting a medical instrument including: a support arm having a first end, a second end, and a chamber extending from the first end to the second end, the support arm defining a longitudinal axis; a support part arranged at the second end of the support arm; a ball joint arranged at the first end of the support arm and including a ball head and a ball seat; a connecting component connected to the ball head and configured for connection with a medical instrument; and a locking device including an operation element and a locking element movably arranged in the chamber and operable by the operation element in a direction in which the ball head is locked by the locking element. The support arm apparatus enables the medical instrument to be flexibly adjusted in position and orientation.

23 Claims, 3 Drawing Sheets

(56) References Cited

U.S. PATENT DOCUMENTS

| | | | |
|---|---|---|---|
| 5,609,565 A * | 3/1997 | Nakamura | A61B 90/50 403/56 |
| 5,918,844 A * | 7/1999 | Ognier | F16M 13/022 269/74 |
| 6,063,021 A * | 5/2000 | Hossain | A61B 17/0218 600/37 |
| 6,491,273 B2 | 12/2002 | King et al. | |
| 6,514,239 B2 * | 2/2003 | Shimmura | A61B 90/50 606/1 |
| 6,575,653 B1 | 6/2003 | Kraeuter | |
| 7,189,246 B2 * | 3/2007 | Otsuka | A61B 90/50 600/102 |
| 7,250,028 B2 * | 7/2007 | Julian | A61B 17/1327 600/235 |
| 8,322,342 B2 * | 12/2012 | Soto | A61G 13/0072 128/845 |
| 9,615,564 B2 * | 4/2017 | Liney | A01K 97/10 |
| 9,700,376 B2 | 7/2017 | Scott et al. | |
| 10,386,049 B2 * | 8/2019 | Yu | F21V 33/0012 |
| 10,788,160 B2 * | 9/2020 | Elias | F16M 11/2021 |
| 10,835,345 B2 * | 11/2020 | Billard | A61B 90/50 |
| 2002/0000503 A1 * | 1/2002 | Fidler | F16C 11/106 403/90 |
| 2007/0282311 A1 * | 12/2007 | Scott | F16M 13/022 606/1 |
| 2011/0315843 A1 | 12/2011 | Hung | |
| 2014/0084761 A1 | 3/2014 | Scott et al. | |
| 2015/0133958 A1 | 5/2015 | Singh et al. | |
| 2016/0341243 A1 * | 11/2016 | Ingrassia | F16M 11/14 |
| 2017/0065366 A1 | 3/2017 | Chauvette et al. | |
| 2018/0116758 A1 | 5/2018 | Schlosser et al. | |

FOREIGN PATENT DOCUMENTS

| | | |
|---|---|---|
| CN | 104983468 A | 10/2015 |
| CN | 105476703 A | 4/2016 |
| CN | 208331642 U | 1/2019 |
| JP | S63280911 A | 11/1988 |
| RU | 185415 U1 | 12/2018 |
| WO | WO 2006/105673 A1 | 10/2006 |
| WO | 2016160272 A1 | 10/2016 |

* cited by examiner

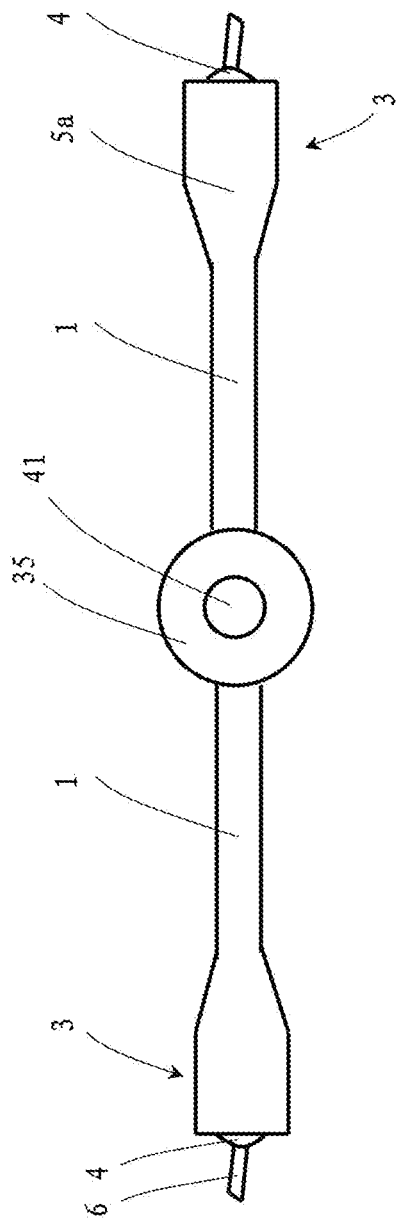
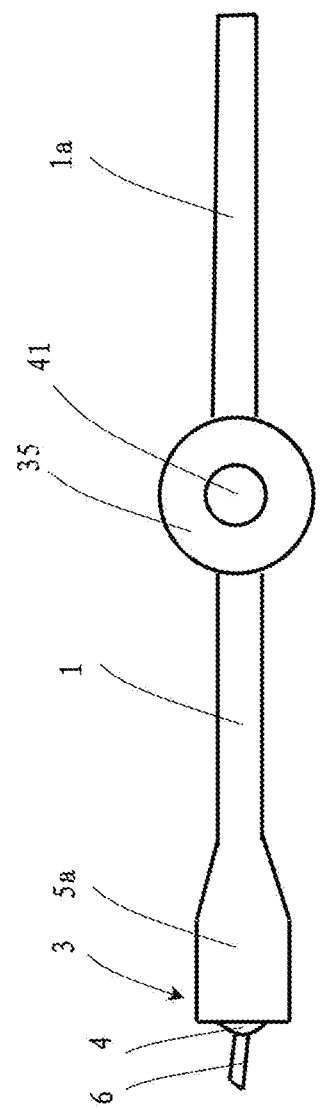
Fig. 2
Fig. 3

SUPPORT ARM APPARATUS FOR SUPPORTING MEDICAL INSTRUMENT

CROSS REFERENCE TO RELATED APPLICATIONS

This application is a 371 U.S. national phase of PCT international patent application number PCT/CN2020/072579, filed Jan. 17, 2020, which claims benefit and priority to Chinese patent application number 201910061209.1 filed Jan. 23, 2019. The disclosure of each aforementioned application is incorporated by reference herein in their entirety. Specifically, PCT international patent application number PCT/CN2020/072579 is incorporated by reference herein in its entirety. And, Chinese patent application number 201910061209.1 is incorporated by reference herein in its entirety.

TECHNICAL FIELD

The present invention relates to a support arm apparatus for supporting a medical instrument.

BACKGROUND ART

Some medical instruments need to be fixed in a proper position and orientation in use. Medical instruments may also need to be adjusted in position and orientation during use. For example, some medical instruments are connected with a pipeline and a cable, and sometimes might be located in a position and orientation that are not advantageous to a diagnosis of a doctor for a patient, wherein an adjustment of the medical instrument is desirable. A medical instrument may be a single instrument, or may be a set of instruments, such as a medical lighting device, a blood sampling pump, a medical probe, a diagnostic glass, and so on.

The patent literature CN104736077B describes a resettable medical instrument support system, including a frame, a ball joint, a frame mounting arm, a sliding joint, a connecting arm, and a connector. Such a support system is complex in structure, large in number of components, and not easy to adjust.

SUMMARY OF INVENTION

An object of the present invention is to provide a support arm apparatus for supporting a medical instrument, which has a simple structure and allows a simple adjustment of the medical instrument connected to the support arm apparatus.

For this purpose, a support arm apparatus for supporting a medical instrument is proposed, including:
- a support arm having a first end, a second end, and a chamber extending from the first end to the second end, the support arm defining a longitudinal axis;
- a ball joint arranged at the first end of the support arm and including a ball head and a ball seat;
- a support part arranged at the second end of the support arm;
- a connecting component connected to the ball head of the ball joint and configured for connection with the medical instrument; and
- a locking device including an operation element and a locking element movably arranged in the chamber and operable by the operation element in a direction in which the ball head is locked by the locking element, for example, by means of friction locking or form locking.

In some embodiments, the support arm may be a straight arm. In some other embodiments, the support arm may be a curved arm, for example, an arc-shaped arm. In some embodiments, the support arm apparatus may include exact one support arm. In some other embodiments, the support arm apparatus may include a plurality of support arms.

In some embodiments, the ball seat may include a sleeve that may have a front stop for the ball head and that may be mounted at the first end of the support arm in such a manner that it may be rotatable about the longitudinal axis but not movable axially relative to the support arm. In some other embodiments, the sleeve may be fixed to the support arm. For example, the sleeve may be integrally formed with the support arm, or may be connected to the support arm by screwing, welding or in other manners.

In some embodiments, the rotation of the sleeve about the longitudinal axis relative to the support arm can be locked, for example, by friction locking or form locking.

In some embodiments, the stop may have a friction surface for contact with the ball head, wherein the ball head can be pressed by the locking element against the friction surface of the stop, so that the rotation of the sleeve about the longitudinal axis of the support arm is frictionally locked.

In some embodiments, the sleeve may have a friction surface, and the locking element may have a counter friction surface, which two friction surfaces can frictionally lock the sleeve when pressed against each other.

In some embodiments, the support arm apparatus may include a thrust element, which may be provided at the first end of the support arm and configured to make the sleeve not movable axially relative to the support arm.

In some embodiments, the sleeve may include a first sleeve section fitted over the support arm, and a second sleeve section connected to the first sleeve section through a connecting element. In some other embodiments, the sleeve may be longitudinally split. In some other embodiments, the sleeve may be in one piece.

In other embodiments, an annular chamber may be formed between the first sleeve section and the support arm, in which annular chamber the connecting element may be received.

In other embodiments, the first sleeve section and the second sleeve section may each have an internal thread, the connecting element may have an external thread, wherein the internal thread of the first sleeve section and the internal thread of the second sleeve section may be screwed to the external thread of the connecting element.

In some embodiments, the connecting element may be fitted over the support arm, and the support arm apparatus may include a thrust element, which may be provided at the first end of the support arm and configured to make the connecting element together with the sleeve not movable axially relative to the support arm.

In some embodiments, the locking element may be configured as a push rod, which may include a rear end operable by the operation element and a front end for cooperation with the ball head, wherein the front end may be provided with a friction surface for contact with the ball head. In some other embodiments, the locking element may be a flexible pull element.

In some other embodiments, the locking element may include a form-locking element, for example, a pin for cooperation with a mesh.

In some embodiments, the front end of the push rod may be provided with a planar friction lining forming the friction surface of the front end.

In some embodiments, the friction lining may be configured to be partially spherical, and can fully contact the ball head.

In some embodiments, the front end of the push rod can be supported at the first end of the support arm in an axial direction of the support arm, and the friction surface of the front end forms a support surface for the ball head.

In some embodiments, a spring may be provided in the chamber of the support arm, with one end of the spring being supported on the support arm and with the other end of the spring being supported on the locking element, wherein the spring biases the locking element towards the ball head.

In some embodiments, the support arm may be fixedly connected to the support part, for example, they may be connected by screwing or welding, or may be integrally formed. In some other embodiments, the support arm is movable relative to the support part.

In some embodiments, the support arm is pivotable relative to the support part, wherein the support part defines a pivot axis.

In some embodiments, the pivot axis is orthogonal to the longitudinal axis. However, it would be appreciated that the pivot axis and the longitudinal axis may also be not coplanar and/or not orthogonal.

In some embodiments, the support arm may include a receiving component at the second end, which may receive the support part.

In some embodiments, the receiving component may have a first hole, and the support part may have a rod rotatably received in the first hole, wherein a longitudinal axis of the rod defines the pivot axis.

In some embodiments, the receiving component may have a second hole, in which the operation element is received.

In some embodiments, the receiving component may have a second hole, in which the operation element may be received.

In some embodiments, the first hole and the second hole may be adjacent to each other.

In some embodiments, the second hole may have a diameter larger than a diameter of the first hole.

In some embodiments, a rod of the support part may extend into the second hole.

In some embodiments, the receiving component may be configured as a cylindrical component.

In some embodiments, the pivotal movement of the support arm relative to the support part can be locked.

In some embodiments, the pivotal movement of the support arm relative to the support part can be locked by the operation element.

In some embodiments, the pivotal movement of the support arm relative to the support part can be frictionally locked by the operation element.

In some embodiments, the support part may include a connector, which may be configured for connection with an external counter connector.

In some embodiments, the connector of the support part may be a plug, and the counter connector may be a socket. In some other embodiments, an inverse arrangement of the plug and the socket is also possible. In some other embodiments, the connector may be a threaded connector, the counter connector may be a threaded hole, and the threaded connector may be screwed into the threaded hole.

In some embodiments, the plug may have a polygonal cross-section, such as a hexagonal cross-section.

In some embodiments, the support arm apparatus may include a locker configured to releasably lock the plug-in connection between the plug and the socket. However, it would be appreciated that the locker may also be arranged on a medical device, for example, on a medical table or a monitoring apparatus.

In some embodiments, the locker may be configured as a button device including a button head. By pressing the button head, the locker can be switched between a locked state, in which the plug-in connection between the plug and the socket can be locked, and a released state, in which the plug-in connection between the plug and the socket can be released. In some other embodiments, the locker may be configured as a knob.

In some embodiments, the button device may include a button rod connected to the button head or having the button head, wherein the button rod is biased at an initial position and can be pressed from the initial position to a predetermined pressed position, wherein the initial position corresponds to the locked state of the locker, and the pressed position corresponds to the released state of the locker.

In some embodiments, the button device may be configured in the principle of a button switch, that is to say, in each time when the button switch is pressed and then released, the button switch switches between the switch-on and switch-off states.

In some embodiments, the button device may include a movable element received in a hole of the plug. The button rod may have a radial protrusion. In the initial position of the button rod, the movable element is pressed by the radial protrusion and thus protrudes from a surface of the socket, and in the pressed position of the button rod, the radial protrusion is disengaged with the movable element. In some embodiments, the movable element may be a pin.

In some embodiments, the button rod may penetrate the operation element.

In some embodiments, the operation element may be configured as a knob. In some other embodiments, the operation element may be configured as a button. In some embodiments, the operation element may be configured as a press element or a pull element that can press or pull the locking element.

In some embodiments, the operation element may be a mechanical or electrical operation element. For example, it is possible that the operation element actuates the locking element by an electromagnetic force.

In some embodiments, the knob may have a rod which may have a threaded hole, and the support part may have a rod which may have an external thread.

In some embodiments, the operation element may have a step surface that can press the support arm against the support part, whereby the pivotal movement of the support arm relative to the support part can be frictionally locked. For example, the step surface can press an end surface of a cylindrical component of the support arm.

In some embodiments, the operation element may have an inclined surface configured to cooperate with a rear end of the locking element, wherein an operating stroke of the operation element can be converted into a displacing stroke of the locking element through the inclined surface.

In some embodiments, the operation element may have a groove, and the support arm may have a limiting element extending into the groove and configured to limit an operating stroke of the operation element. For example, the limiting element may be a pin.

In some embodiments, the support arm apparatus may include exact one support arm, or may include a plurality of support arms.

In some embodiments, the plurality of support arms may have a common operation element.

In some embodiments, the medical instrument may be a blood pump.

It should also be pointed out that the technical features in the present application can be combined arbitrarily, so far as they are not mutually contradictory. All technically possible combinations of the features are technical contents contained in the disclosure.

BRIEF DESCRIPTION OF THE DRAWINGS

The present invention will be explained in more detail with reference to the drawings with the aid of specific embodiments. Among the schematic drawings:

FIG. 2 is a largely simplified top view of a support arm apparatus according to another embodiment of the present invention;

FIG. 3 is a largely simplified top view of a support arm apparatus according to a further embodiment of the present invention.

DETAILED DESCRIPTION OF THE DRAWINGS

Figure 1:
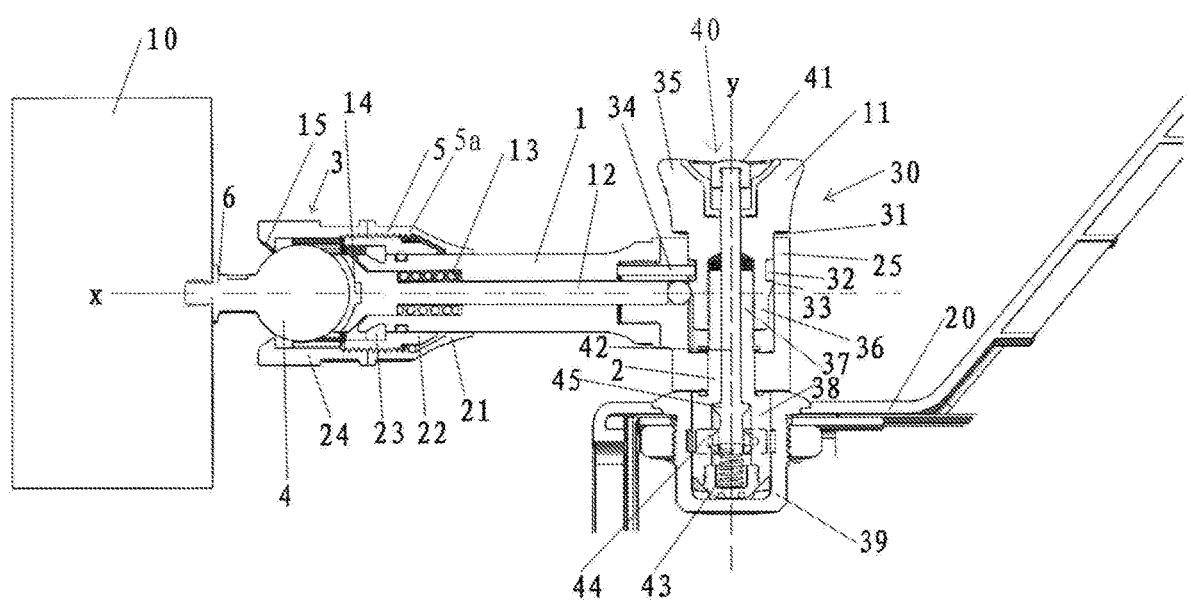
FIG. 1 is a cross-sectional view of a support arm apparatus according to an embodiment of the present invention.

FIG. 1 is a cross-sectional view of a support arm apparatus according to an embodiment of the present invention. The support arm apparatus is mounted on a medical table 20 shown partially. The support arm apparatus includes a connector 38 configured as a plug. The medical table 20 may include one or more counter connectors 39 configured as a socket. The plug may be associated with a locker 40, by which the plug can be locked in the socket. When the locker 40 is released, the plug can be pulled out of the socket. A specific structure of the locker 40 will be described in more detail below. The support arm apparatus may be placed on any suitable device. For example, it may be placed on a hospital bed, an operating table, an in vitro tester, a wall, a bracket, etc., so far as these devices have corresponding counter connectors.

This support arm apparatus includes a support arm 1 having a first end, a second end and a chamber extending from the first end to the second end, wherein the support arm defines a longitudinal axis x. The support arm apparatus includes a support part 2 arranged at the second end of the support arm 1. The support arm apparatus includes a ball joint 3 arranged at the first end of the support arm 1 and including a ball head 4 and a ball seat 5. The support arm apparatus includes a connecting component 6, which is connected with the ball head 4 of the ball joint 3 and is configured for connection with a medical instrument 10. The support arm apparatus includes a locking device 30 having an operation element 11 and a locking element 12 that is movably arranged in the chamber and is operable by the operation element in a direction in which the ball head is locked by the locking element.

The medical instrument 10 is only shown schematically in FIG. 1. For example, one or more medical instruments may be kept in a holder that may be in threaded connection to the connecting component 6. The medical instrument may be, for example, a blood sampling pump, a lightening device, a probe or the like.

The ball seat 5 includes a sleeve 5a having a front stop 15 for the ball head 4. The sleeve may be mounted at the first end of the support arm 1 in such a manner that it may be rotatable about the longitudinal axis x but not movable axially relative to the support arm 1. The stop 15 has a friction surface for contact with the ball head 4, and the ball head 4 can be pressed by the locking element 12 against the friction surface of the stop 15, so that the rotation of the sleeve 5a about the longitudinal axis x of the support arm 1 is frictionally locked. The sleeve 5a includes a first sleeve section 21 and a second sleeve section 24, wherein the first sleeve section is fitted over the support arm 1, and the first sleeve section 21 and the second sleeve section 24 are connected to each other through a connecting element 22. An annular chamber is formed between the first sleeve section 21 and the support arm 1, in which annular chamber the connecting element 22 is received. The first sleeve section 21 and the second sleeve section 24 each have an internal thread, and the connecting element 22 has an external thread, wherein the internal thread of the first sleeve section 21 and the internal thread of the second sleeve section 24 is screwed to the external thread of the connecting element 22. The connecting element 22 is fitted over the support arm 1, and a thrust element 23 is provided at the first end of the support arm 1 and is configured to make the connecting element 22 together with the sleeve 5a not movable axially relative to the support arm 1.

The locking element 12 is configured as a push rod having a rear end operable by the operation element 11 and a front end for cooperation with the ball head 4, wherein the front end is provided with a planar friction lining 14. The friction lining 14 is configured to be partially spherical and can fully contact the ball head 4. The front end of the push rod can be supported at the first end of the support arm 1 in an axial direction of the support arm 1, and the friction surface of the front end forms a support surface for the ball head 4. A spring 13 is provided in the chamber of the support arm 1, with one end of the spring being supported on the support arm 1 and with the other end of the spring being supported on the locking element 12. The spring biases the locking element 12 towards the ball head 4. Therefore, even if the operation element 11 is in a released state, the rotation of the ball head 4 or the sleeve 5a needs to overcome a predetermined small resistant force.

The support arm 1 is pivotable relative to the support part 2. The support arm 1 is provided at the second end with a receiving component 25, which is configured as a cylindrical component to receive the support part 2. The receiving component 25 has a first hole, and the support part 2 has a rod 37 rotatably received in the first hole, wherein a longitudinal axis of the rod defines a pivot axis y. The pivot axis y and the longitudinal axis x are orthogonal to each other and lie in a common plane. The receiving component 25 has a second hole, in which the operation element 11 is received. The first hole and the second hole are adjacent to each other, and the second hole has a diameter larger than a diameter of the first hole. The rod 37 of the support part 2 extends into the second hole.

The operation element 11 is configured as a knob. The knob has a head 35 and a rod 36. The head 35 may be rotated by hand, and as an alternative or supplement, it may be rotated with a tool, such as a wrench. The rod 36 of the knob has a threaded hole, and the rod 37 of the support part 2 has an external thread. By the rotation of the head 35, the operation element 11 can approach or leave away from the support part. The operation element 11 has a step surface 31, which approaches or leaves away from an upper end surface of the receiving component 25 by the rotation of the head 35. When the step surface 31 presses said end surface, the receiving component is pressed against an end surface of the counter connector 39, with a result that the pivotal movement of the receiving component 25 and thus the support arm 1 about the pivot axis y is frictionally locked.

The operation element 11 has an inclined surface 33 configured to cooperate with the rear end of the locking element 12, wherein an operating stroke of the operation element can be converted into a displacing stroke of the locking element 12 through the inclined surface 33. When the head 35 is rotated, the inclined surface 33 moves upward or downward along with the head 35. The inclined surface 33 may be configured as a surrounding inclined surface.

The operation element 11 is provided with a groove 32 adjacent to the inclined surface 33, and the support arm 1 has a limiting element 34 extending into the groove, wherein the limiting element is configured to limit the operating stroke of the operation element 11.

The support arm apparatus may include a locker 40 configured to releasably lock the plug-in connection between the plug and the socket. As shown in FIG. 1, the locker 40 is configured as a button device. The button device includes a button head 41, wherein by pressing the button head the locker 40 can be switched between a locked state, where the plug-in connection between the plug and the socket can be locked, and a released state, where the plug-in connection between the plug and the socket can be released. The button device further includes a button rod 42 connected to the button head 41, which is biased in an initial position by a spring element 43 and can be pressed from the initial position to a predetermined pressed position, wherein the initial position corresponds to the locked state of the locker 40 and the pressed position corresponds to the released state of the locker 40. The button rod 42 has a stop 45 for defining the initial position. The button rod 42 is received in a chamber of the support part 2, extends upward until it penetrates the operation element 11 and is exposed from an end surface of the operation element 11. The button head 41 is located within a recess in the end surface of the operation element 11 and allows for a pressing operation. The button device includes a movable element received in a hole 44 of the plug. The button rod 42 has a radial protrusion. In the initial position of the button rod 42, the movable element is pressed by the radial protrusion and hence protrudes from a surface of the socket, and in the pressed position of the button rod, the radial protrusion is disengaged with the movable element. For the sake of clarity, the movable element is not shown in FIG. 1 so that the recess in the socket for the movable element can be better observed. The movable element may be, for example, a pin.

In the embodiment shown in FIG. 1, the rotational movement of the ball head 4, the rotational movement of the sleeve 5a about the longitudinal axis x, and the pivotal movement of the support arm 1 about the pivot axis y can be locked and released by the same one operation element 11.

FIG. 2 is a largely simplified top view of a support arm apparatus according to another embodiment of the present invention. The support arm apparatus includes two support arms 1, wherein each support arm 1 and various components such as a locking element 12, a spring 13, a friction lining 14, a ball head 4, a sleeve 5a, a thrust element 23, a connecting element 22 and so on that are received in the support arm, may be configured in the same or similar manner as those in the embodiment shown in FIG. 1. The same reference signs represent the same components. For components not shown in FIG. 2, reference may be made to FIG. 1 and the detailed description with respect to FIG. 1.

In some embodiments not shown, two support arms 1 may have a common support part 2 and a common receiving component 25, which may be configured in the same or similar manner as those in the embodiment shown in FIG. 1. Therefore, the operation element 11 and the locker 40 may also be configured in the same or similar manner as those in the embodiment shown in FIG. 1. Therefore, the two support arms 1 can commonly pivot about the pivot axis y, the two ball heads 4 can rotate respectively, and the two sleeves 5a can rotate about the longitudinal axes x of the respective support arms as well. The rotational movement of the two ball heads 4, the rotational movement of the two sleeves 5a about the longitudinal axes x, and the common pivotal movement of two support arms 1 about the pivot axis y can be locked and released by the same one operation element 11.

In some embodiments not shown, two support arms 1 may have a common support part 2 and have their respective receiving components 25. The two receiving components 25 overlap each other and are fitted over the rod 37 of the support part 2. This situation may be so described that the rod 37 shown in FIG. 1 is extended upward, and an additional receiving component 25 is provided between the receiving component 25 and the operation element 11 shown in FIG. 1. As a result, the two support arms 1 can independently pivot about the pivot axis y, the two ball heads 4 can rotate respectively, and the two sleeves 5a can rotate about the longitudinal axes x of the respective support arms. The rotational movement of the two ball heads 4, the rotational movement of the two sleeves 5a about the longitudinal axes x, and the respective pivotal movement of the two support arms 1 about the pivot axis y can be locked and released by the same one operation element 11.

In the embodiment shown in FIG. 2, two support arms 1 are arranged at an angle of 180 degrees. Of course, they may also be arranged at another angle, such as at an angle of 60, 90 or 120 degrees. Besides, more support arms 1 may also be provided. For example, three support arms 1 may be spaced from each other at an angular distance of 120 degrees around the common receiving component 25.

FIG. 3 is a largely simplified top view of a support arm apparatus according to a further embodiment of the present invention. The support arm apparatus includes a support arm 1 and an additional arm 1a. Except the additional arm 1a, the remaining support arm apparatus according to FIG. 3 may be configured in the same or similar manner as that according to FIG. 1. The additional arm 1a is a rod fixed to the receiving component 25 of the support arm 1, and for example may be used for hanging an object. In the embodiment shown in FIG. 3, the support arm 1 and the additional arm 1a are arranged at an angle of 180 degrees, so that the arm 1a may be regarded as an extension of the support arm 1, especially in the case where the arm 1a and the support arm 1 have the same cross-section and are in a straight line. In other words, the support part 2 defines the position of the second end of the support arm 1, and a portion of the support arm 1 that exceeds the support part 2 in the direction away from the first end, even if it is an integral portion of the support arm 1, may be regarded as an extension of the support arm.

Of course, they may also be arranged at another angle, such as at an angle of 60, 90 or 120 degrees. In some embodiments not shown, a combination of one or more support arms 1 and one or more additional arms 1a is also possible.

Figure 4:
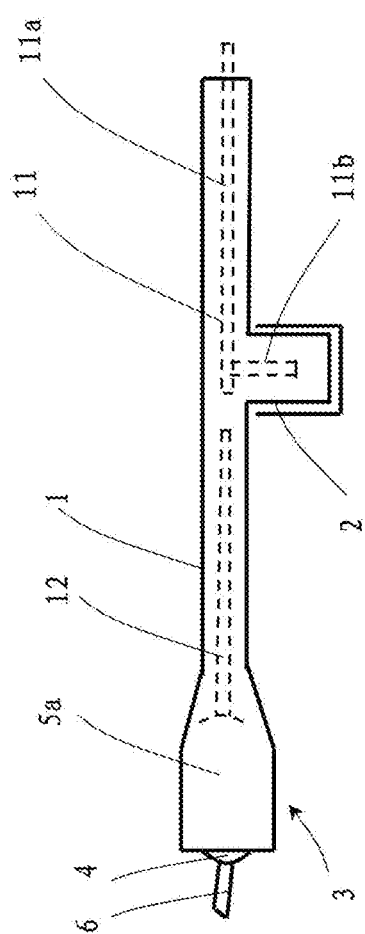
FIG. 4 is a largely simplified side view of a support arm apparatus according to another embodiment of the present invention.

FIG. 4 is a largely simplified side view of a support arm apparatus according to an additional embodiment of the present invention. The support arm apparatus includes a support arm 1, a ball joint 3 and a support part 2. The ball joint 3 and components received in the support arm 1 may be configured in the same or similar manner as those in the embodiment of FIG. 1. The support part 2 is fixedly connected, for example, made in one piece with the support arm 1. A locking element 12 received in the support arm 1, and an operation element 11 received in an extension of the support arm 1 (or to say an additional arm) and in a support part 2 are indicated by dashed lines respectively. The operation element 11 includes a first portion 11a received in the extension and a second portion 11b received in the support part 2. The support part 2 may be rotatably inserted into a recess of a medical device, which recess has an inner circumferential surface as a friction surface. A movable friction element (not shown) is received in a wall of the support part 2. When the operation element 11 is pressed towards the locking element 12, the first portion 11a is pressed against the locking element so that the ball head 4 and the sleeve 5a are frictionally locked, and meanwhile the second portion 11b presses the movable friction element against an inner circumferential surface of the recess, with a result that the pivotal movement of the support part 2 relative to the recess is also frictionally locked. The recess may be provided with a button device (not shown) to prevent the support part 2 from being pulled out of the recess.

Finally, it should be pointed out, the present invention is not limited to the specific embodiments that have been shown and described above. Modifications and variations may be made by those skilled in the art on the basis of these embodiments, and they fall into the protection scope of the present invention.

What is claimed is:

1. A support arm apparatus for supporting a medical instrument, the support arm apparatus comprising:
   a support arm having a first end, a second end, and a chamber extending from the first end to the second end, the support arm defining a longitudinal axis;
   a ball joint arranged at the first end of the support arm and including a ball head and a ball seat;
   a support part arranged at the second end of the support arm, wherein the support part has a connector configured for connection with an external counter connector, and wherein the connector of the support part is one of a plug or a socket, and the counter connector is the other of the plug or the socket;
   a connecting component connected to the ball head and configured for connection with the medical instrument;
   a locking device including an operation element and a locking element movably arranged in the chamber and operable by the operation element in a direction in which the ball head is locked by the locking element; and
   a locker configured to releasably lock a plug-in connection between the plug and the socket, wherein the locker is configured as a button device comprising a button head, and wherein by pressing the button head, the locker is switchable between a locked state, where the plug-in connection between the plug and the socket is lockable and a released state, where the plug-in connection between the plug and the socket is releasable.

2. The support arm apparatus of claim 1, wherein:
   the ball seat includes a sleeve having a front stop for the ball head;
   the sleeve is mounted at the first end of the support arm in such a manner that it is rotatable about the longitudinal axis but not movable axially relative to the support arm; and
   the rotation of the sleeve about the longitudinal axis relative to the support is lockable.

3. The support arm apparatus of claim 2, wherein:
   the stop has a friction surface for contact with the ball head; and
   the ball head is configured to be pressed by the locking element against the friction surface of the stop, so that the rotation of the sleeve about the longitudinal axis of the support arm is frictionally locked.

4. The support arm apparatus of claim 2, wherein the support arm apparatus includes a thrust element arranged at the first end of the support arm and configured to make the sleeve not movable axially relative to the support arm.

5. The support arm apparatus of claim 2, wherein:
   the sleeve includes a first sleeve section and a second sleeve section;
   the first sleeve section is fitted over the support arm; and
   the first sleeve section and the second sleeve section are connected to each other through a connecting element.

6. The support arm apparatus of claim 5, wherein:
   the first sleeve section and the second sleeve section each have an internal thread;
   the connecting element has an external thread; and
   the internal thread of the first sleeve section and the internal thread of the second sleeve section are screwed to the external thread of the connecting element.

7. The support arm apparatus of claim 5, wherein the connecting element is fitted over the support arm, and the support arm apparatus includes a thrust element arranged at the first end of the support arm and configured to make the connecting element together with the sleeve not movable axially relative to the support arm.

8. The support arm apparatus of claim 1, wherein:
   the locking element is configured as a push rod having a rear end operable by the operation element and a front end for cooperation with the ball head; and
   the front end is provided with a friction surface for contact with the ball head.

9. The support arm apparatus of claim 8, wherein the front end of the push rod is provided with a planar friction lining, which forms the friction surface of the front end.

10. The support arm apparatus of claim 9, wherein the friction lining is configured to be partially spherical and ean-fully contact the ball head.

11. The support arm apparatus of claim 1, wherein:
   a spring is provided in the chamber of the support arm, with one end of the spring being supported on the support arm and with the other end of the spring being supported on the locking element; and
   the spring biases the locking element towards the ball head.

12. The support arm apparatus of claim 1, wherein:
   the support arm is pivotable relative to the support part;
   the support part defines a pivot axis; and
   pivotal movement of the support arm relative to the support part is lockable.

13. The support arm apparatus of claim 12, wherein:
   the support arm includes a receiving component at the second end that receives the support part;
   the receiving component has a first hole;
   the support part has a rod rotatably received in the first hole; and
   a longitudinal axis of the rod defines the pivot axis.

14. The support arm apparatus of claim 13, wherein the receiving component has a second hole, in which the operation element is received.

15. The support arm apparatus of claim 14, wherein the rod of the support part extends into the second hole, the operation element is configured as a knob, the knob has a rod with a threaded hole, the support part has a rod with an external thread, the first hole and the second hole are adjacent to each other, and the second hole has a diameter larger than a diameter of the first hole.

16. The support arm apparatus of claim 1, wherein:
the button device includes a button rod connected with the button head or having the button head;
the button rod is biased in an initial position and configured to be pressed from the initial position to a predetermined pressed position; and
the initial position corresponds to the locked state of the locker and the pressed position corresponds to the released state of the locker.

17. The support arm apparatus of claim 16, wherein:
the button device includes a movable element received in a hole of the plug, and the button rod has a radial protrusion; and
in the initial position of the button rod, the movable element is pressed by the radial protrusion and thus protrudes from a surface of the socket, and in the pressed position of the button rod, the radial protrusion is disengaged with the movable element.

18. The support arm apparatus of claim 17, wherein the button rod penetrates the operation element.

19. The support arm apparatus of claim 12, wherein the operation element has a step surface configured to press the support arm against the support part, whereby the pivotal movement of the support arm relative to the support part are frictionally lockable.

20. The support arm apparatus of claim 1, wherein:
the operation element has an inclined surface configured to cooperate with a rear end of the locking element; and
an operating stroke of the operation element is convertible into a displacing stroke of the locking element through the inclined surface.

21. The support arm apparatus of claim 1, wherein the operation element has a groove, and the support arm has a limiting element extending into the groove and configured to limit the operating stroke of the operation element.

22. The support arm apparatus of claim 1, wherein the support arm apparatus includes exactly one support arm, or includes a plurality of support arms associated with the same one operation element.

23. The support arm apparatus of claim 1, wherein the medical instrument is a blood pump.

* * * * *